(12) United States Patent
Monguzzi et al.

(10) Patent No.: US 7,071,329 B2
(45) Date of Patent: Jul. 4, 2006

(54) PROCESS FOR PREPARING CEPHALOSPORINS WITH SALIFIED INTERMEDIATE

(75) Inventors: Riccardo Monguzzi, Dorio (IT); Antonio Manca, Milan (IT); Leonardo Marsili, Brescia (IT); Maurizio Zenoni, Paullo (IT)

(73) Assignee: ACS Dobfar S.p.A., Tribiano (IT)

( * ) Notice: Subject to any disclaimer, the term of this patent is extended or adjusted under 35 U.S.C. 154(b) by 151 days.

(21) Appl. No.: 10/916,532

(22) Filed: Aug. 12, 2004

(65) Prior Publication Data

US 2005/0119478 A1   Jun. 2, 2005

Related U.S. Application Data

(63) Continuation-in-part of application No. 10/821,986, filed on Apr. 12, 2004, now abandoned.

(30) Foreign Application Priority Data

Dec. 2, 2003 (IT) ............... MI2003A2354
Feb. 12, 2004 (IT) ............... MI2004A0233

(51) Int. Cl.
*C07D 501/04* (2006.01)
*C07D 501/36* (2006.01)
*C07D 501/24* (2006.01)

(52) U.S. Cl. ............ 540/226; 540/222; 540/225; 540/228; 540/227

(58) Field of Classification Search ............... None
See application file for complete search history.

(56) References Cited

U.S. PATENT DOCUMENTS 4,458,072 A   7/1984   Reiner et al.

| | | |
|---|---|---|
| 5,583,216 A | 12/1996 | Ochiai et al. |
| 5,705,496 A * | 1/1998 | Polansky .............. 514/204 |
| 6,384,215 B1 | 5/2002 | Deshpande et al. |
| 6,458,949 B1 | 10/2002 | Handa et al. |
| 6,552,186 B1 | 4/2003 | Gerlach et al. |
| 2005/0059820 A1* | 3/2005 | Datta et al. ............ 540/227 |

FOREIGN PATENT DOCUMENTS

| EP | 0 030 294 A2 | 6/1981 |
|---|---|---|
| GB | 2 012 276 A | 7/1979 |

* cited by examiner

*Primary Examiner*—Mark L. Berch
(74) *Attorney, Agent, or Firm*—Oblon, Spivak, McClelland, Maier & Neustadt, P.C.

(57) ABSTRACT

Cephalosporins may be conveniently prepared by a process in which a benzathinium salt of formula (V)

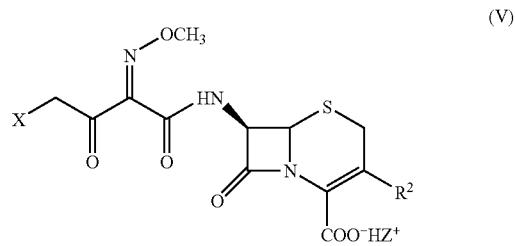

wherein:
Z is benzathine; and X and $R^2$ are as defined in the specification, is reacted with thiourea. The resulting product may be crystallized as a sodium salt, as an internal salt, or as a pharmaceutically acceptable salt.

12 Claims, No Drawings

PROCESS FOR PREPARING CEPHALOSPORINS WITH SALIFIED INTERMEDIATE

CROSS REFERENCES TO RELATED APPLICATIONS

This application is a continuation-in-part of U.S. patent application Ser. No. 10/821,986, filed on Apr. 12, 2004, Now Abandoned and claims priority to Italian Patent Application No. MI2003A 002354, filed on Dec. 2, 2003, and Italian Patent Application No. MI2004A 000233, filed on Feb. 12, 2004, all of which are incorporated herein by reference in their entireties.

BACKGROUND OF THE INVENTION

1. Field of the Invention

The present invention relates to novel processes for preparing various cephalosporins. The present invention further relates to novel intermediates useful for preparing cephalosporins.

2. Discussion of the Background

Numerous cephalosporins of formula (I)

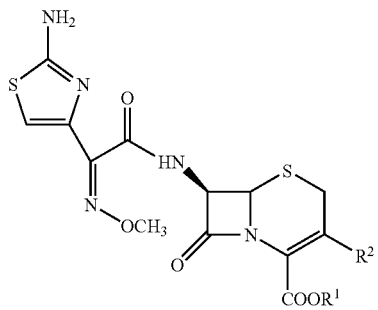

characterized by the presence of a 2-(2-aminothiazol-4-yl)-2-methoxyiminoacetic chain in the 2 position of 7-ACA, and its derivatives of formula (II)

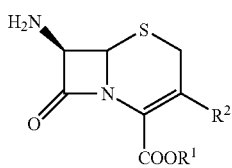

are known in which $R^2$ can have various meanings including $-CH_2OCOCH_3$ in the case of 7-ACA, the cefotaxime nucleus, or

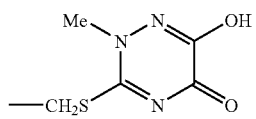

in the case of 7-ACT, the ceftriaxone nucleus, or

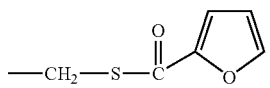

in the case of Furaca, the ceftiofur nucleus.

Each of these cephalosporins, including those having a different meaning of $R^1$ and $R^2$, was independently invented and synthesized with its own synthesis method, so that initially there was no common method suitable for producing all cephalosporins having the 2-(2-aminothiazol-4-yl)-2-methoxyiminoacetic chain.

U.S. Pat. No. 5,583,216 discloses a process for inserting the aforesaid chain into 7-ACA and its derivatives for the production of any cephalosporin included in the aforesaid group. However, the process disclosed in U.S. Pat. No. 5,583,216 cannot be applied industrially for producing cephalosporins.

U.S. Pat. No. 6,458,949 discloses the intermediate of formula (A)

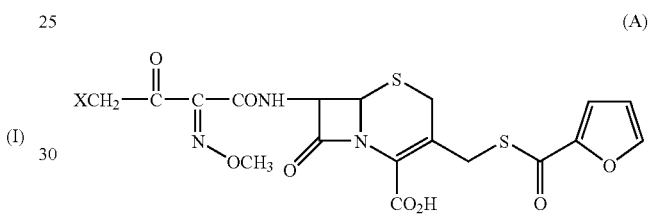

in which X is Cl or Br, and its use for preparing ceftiofur by cyclization with thiourea.

This intermediate is always precipitated in an acid form from a solution in methylene chloride at a temperature of 2 to 5° C., collected by filtration, washed with cold water (5° C.) and then with methylene chloride. In view of the fact that the precipitate originates from a solution in methylene chloride, according to the usual technique it would have been logical to expect the first wash to have been effected with the same solvent, the water wash being effected only later. This reversal of the wash order and the use of cold water are therefore not random, but point to the fact that the intermediate does not possess great stability and that the water-soluble acid impurities which impregnate the solid just filtered off must be rapidly removed. In addition, the intermediate disclosed in U.S. Pat. No. 6,458,949, again in acid form, is dried before subsequent cyclization with thiourea, as this reaction is carried out in water-tetrahydrofuran and it is advisable to remove methylene chloride residues. Moreover the maximum obtainable yield is only 75%.

U.S. Pat. No. 6,552,186 discloses a compound of formula (IV)

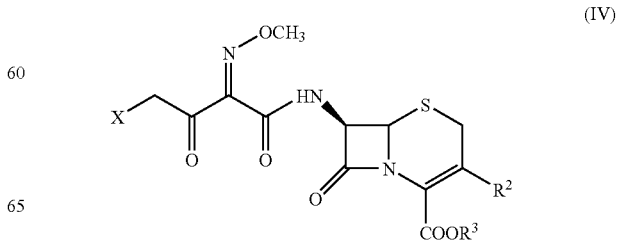

in which X is halogen, R³ is trialkylsilyl and R² is

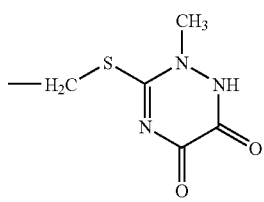

or

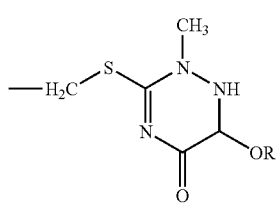

This compound may be reacted with silylated thiourea to provide a compound of formula (I) in which R¹ and R² have the aforesaid meanings and which on subsequent hydrolysis gives the compound having the same formula (I) but in which R¹ is H and R² is as afore-stated, i.e., ceftriaxone.

Thus, U.S. Pat. No. 6,522,186 discloses a compound of formula (IV) in which R³ is trialkylsilyl. The corresponding derivative in which R³ is H, however, had already been disclosed in U.S. Pat. No. 4,458,072 as an amorphous product (see, column 16, line 49) without any indication of the yield, by a laborious process using a precipitating agent such as petroleum ether. The disclosed method is certainly unsuitable for industrial use. Moreover, U.S. Pat. No. 6,552,186 says nothing about yields, as the disclosed process comprises direct formation of the silylated product of formula (IV) and subsequent reaction with silylated thiourea to give silylated ceftriaxone. The final step to obtain ceftriaxone disodium salt takes place by known methods. However, overall total process yields are not given.

U.S. Pat. No. 6,458,949 discloses a process by which Furaca is silylated and then reacted with a compound of formula (III)

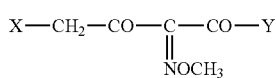

in which X is Cl or Br and Y is Cl, or —O—CH=N⁺(CH₃)₂ Cl⁻ to isolate an afore-stated compound of formula (A), in which X is Cl or Br and the carboxyl is free, non-salified and non-esterified. When reacted with thiourea in a partly aqueous solvent, this intermediate produces ceftiofur.

Compounds of formula (III) have been known for some time. For example, GB 2,012,276 describes in example 5 the preparation of a compound of formula (III) in which the methoxyimino group is substituted by the ethoxyimino group, X is Br and Y is Cl, by reacting the corresponding acid having the same formula (III) but in which X is Br and Y is OH, with PCl₅ in a dichloromethane solution. According to example 13 of GB 2,012,276,7-(4-chloro-3-oxo-2-methoxyiminobutyryl-amino)cephalosporanic acid is subsequently reacted with thiourea to give a sodium salt of 7-[2-(2-aminothiazol-4-yl)-2-methoxyiminoacetamido)cephalosporanic acid, this being cefotaxime, EP 30294 (page 4, lines 36–37 and 40–45), U.S. Pat. No. 6,384,215 (column 3, lines 19–20) and U.S. Pat. No. 6,458,949 (column 4, line 1; column 5, line 2 and lines 47–48) also describe the preparation of compounds having a structure similar to that of formula (III).

It is therefore apparent that compounds of formula (III) in activated form, able to react with a compound of formula (II) silylated at the carboxyl, can be prepared for example as chlorides by reaction with PCl₅ or other chlorinating agents, such as POCl₃ and DMF, in dichloromethane.

However, there remains a need for new methods for producing cephalosporins. There also remains a need for new intermediates which are useful for producing cephalosporins.

SUMMARY OF THE INVENTION

Accordingly, it is one object of the present invention to provide novel processes for preparing cephalosporins.

It is another object of the present invention is to provide a process of high efficiency in terms of final product yield and purity, for producing ceftiofur, cefotaxime, ceftriaxone, and cephalosporins generally, characterized by the same general formula (I)

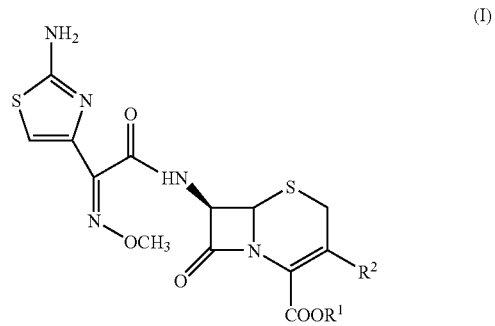

in which R¹ is H or Na and R² is chosen from the group consisting of —H, —CH₃, —CH₂OCH₃, —CH₂OCOCH₃, —CH=CH₂,

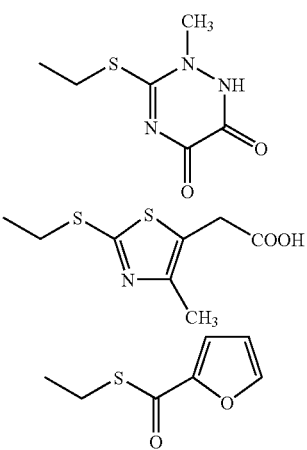

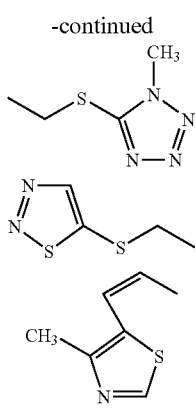

It is another object of the present invention to provide novel intermediates which are useful for preparing cephalosporins.

These and other objects, which will become apparent during the following detailed description, have been achieved by the inventors' discovery that compounds of formula (I) and pharmaceutically acceptable salts thereof

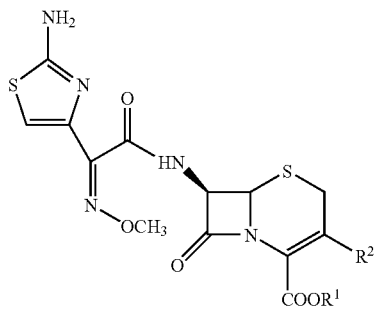

wherein:
R$^1$ is H or Na; and
R$^2$ is selected from the group consisting of

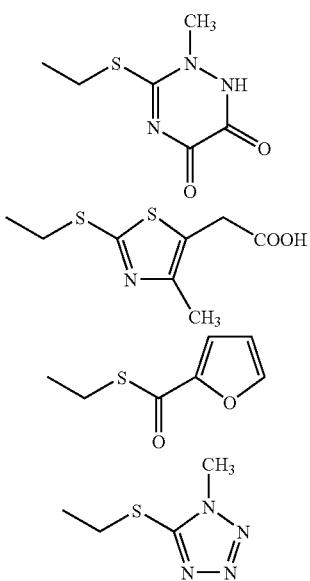

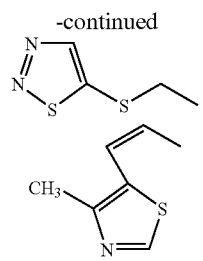

—H, —CH$_3$, —CH$_2$OCH$_3$, —CH$_2$OCOCH$_3$, and —CH=CH$_2$, may be conveniently prepared by a process which comprises:
(1) reacting a compound of formula (IV)

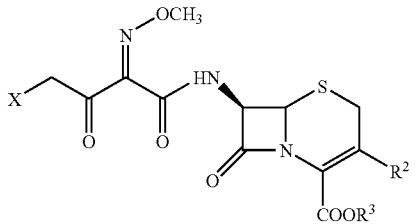

wherein:
X is Cl or Br;
R$^2$ is as defined above; and
R$^3$ is hydrogen,
with benzathine or a salt thereof, to obtain a compound of formula (V)

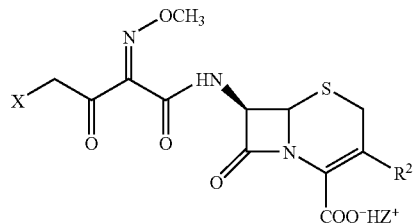

wherein:
Z is benzathine; and
X and R$^2$ are as defined above; and
(2) reacting said compound of formula (V) with thiourea, to obtain said compound of formula (I) or said pharmaceutically acceptable salt thereof.

The inventors have also discovered that compounds of formula (V)

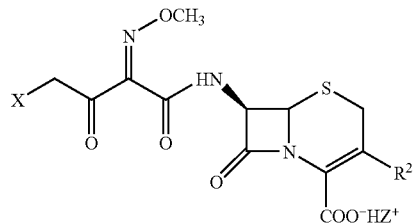

wherein:
Z is benzathine;
X is is Cl or Br; and
R² is selected from the group consisting of

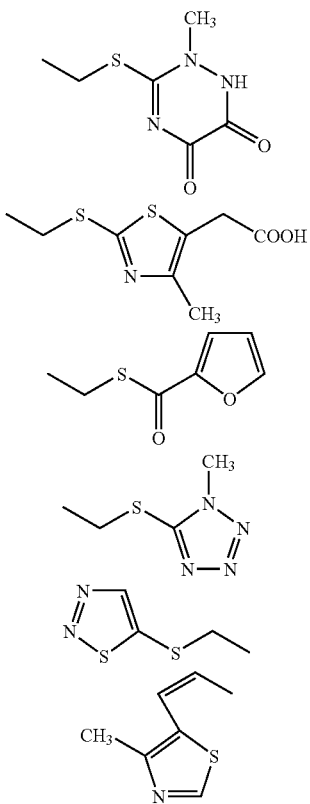

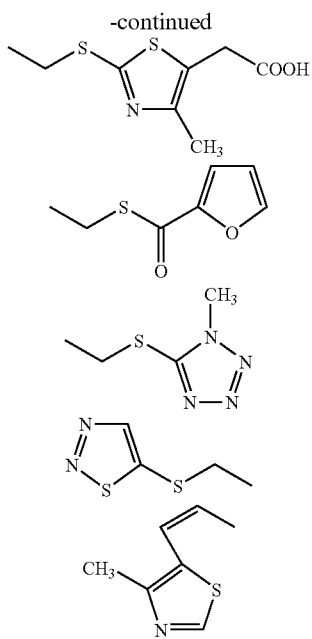

—H, —CH₃, —CH₂OCH₃, —CH₂OCOCH₃, and —CH=CH₂ are useful for preparing cephalosporins.

The inventors have also discovered that compounds of formula (V)

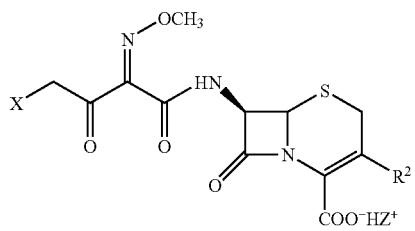
(V)

wherein:
Z is benzathine;
X is is Cl or Br; and
R² is selected from the group consisting of

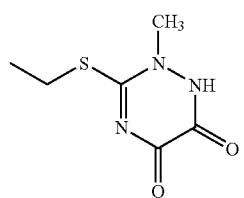

—H, —CH₃, —CH₂OCH₃, —CH₂OCOCH₃, and —CH=CH₂, may be prepared by a process which comprises:

(1) reacting a compound of formula (IV)

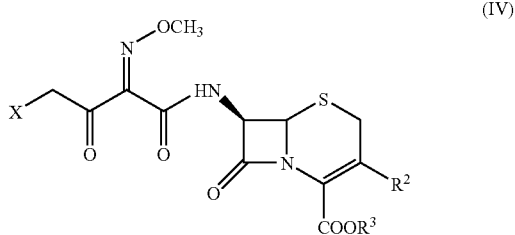
(IV)

wherein X and R² are as defined above with benzathine or a salt thereof, to obtain said compound of formula (V).

Thus, the inventors have discovered that a compound of formula (II)

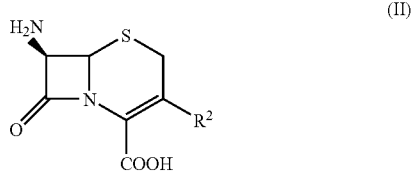
(II)

in which R² has the afore-stated meanings may be silylated at the carboxyl to give the corresponding trialkylsilyl-ester which is then reacted with a compound of formula (III)

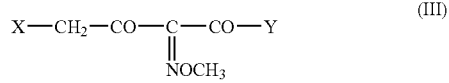
(III)

in which X is Cl or Br and Y is Cl, or —O—CH=N⁺(CH₃)₂ Cl⁻, to give a cephalosporin of formula (IV)

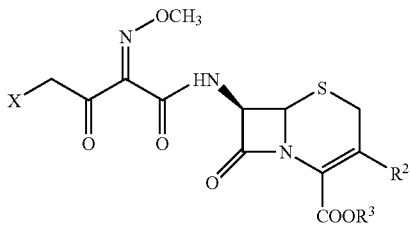

(IV)

in which X and R² have the afore-stated meanings, and R³ is trialkylsilyl, which may then be hydrolyzed at a pH of 7 to 7.5 and then treated in a partly aqueous solution with benzathine or a salt thereof, to obtain crystallization of a new cephalosporin of formula (V)

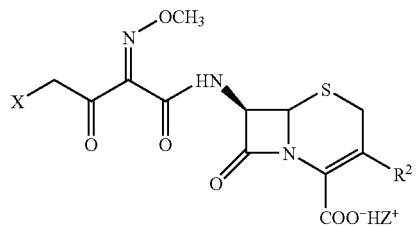

(V)

where Z is benzathine, in which the carboxyl is salified by the benzathine, this salt being filtered off, washed with water and reacted in a partly aqueous solvent with thiourea, to lead to the formation of the 2-(2-aminothiazol-4-yl)-2-methoxy-iminoacetic chain and give a solution of the compound of general formula (I) in which R² has the afore-stated meanings and R¹ is H, the compound of formula (I) being crystallized from this solution in the form of the sodium salt, of the salt of a pharmaceutically acceptable inorganic acid or of an internal salt.

Simultaneously with the formation of the 2-(2-aminothiazol-4-yl)-2-methoxyyminoacetic chain there may be the precipitation of benzathine hydrochloride which is filtered off and removed to leave a very pure solution of the compound of general formula (I).

In particular, it has been surprisingly found possible to quantitatively isolate in aqueous solution a cephalosporin of formula (V), in which R² is —CH₂OCOCH₃, or

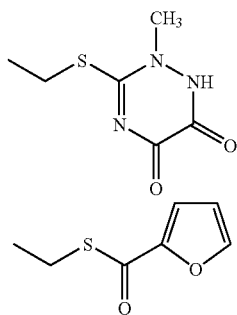

without any interaction with the halogen atom X present in the compounds of formula (V).

This precipitation in aqueous solution automatically eliminates all the acid impurities originating from the preparation of the aforesaid compounds of formula (V). By then simply washing with water, a high purity moist product is obtained ready for subsequent reaction with thiourea in a partly aqueous environment.

A further considerable advantage of the present invention derives from the fact that the cyclization reaction with thiourea, leading to the formation of HCl, finds in benzathine a base able to subtract it from the solution as the hydrochloride insoluble under reaction conditions. In this manner, a solution is obtained which contains only cephalosporin in acid form of such purity as to enable it to be very easily crystallized as the sodium salt, by adding a sodium salt such as sodium acetate or sodium 2-ethyl-hexanoate.

DETAILED DESCRIPTION OF THE PREFERRED EMBODIMENTS

Thus, in a first embodiment, the present invention provides novel processes for preparing a compound of formula (I) or a pharmaceutically acceptable salt thereof

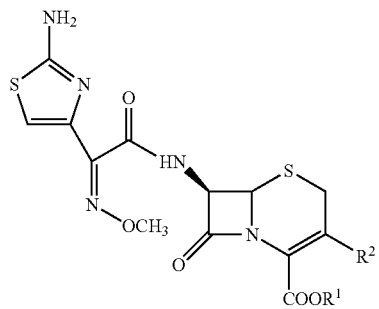

(I)

wherein:

R¹ is H or Na; and

R² is selected from the group consisting of

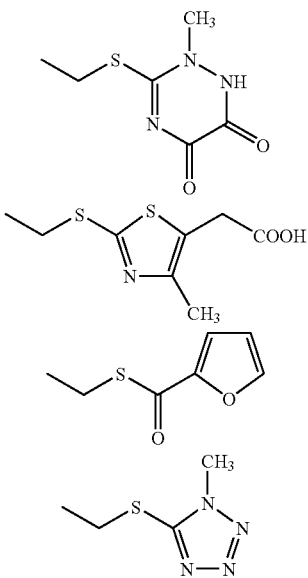

-continued

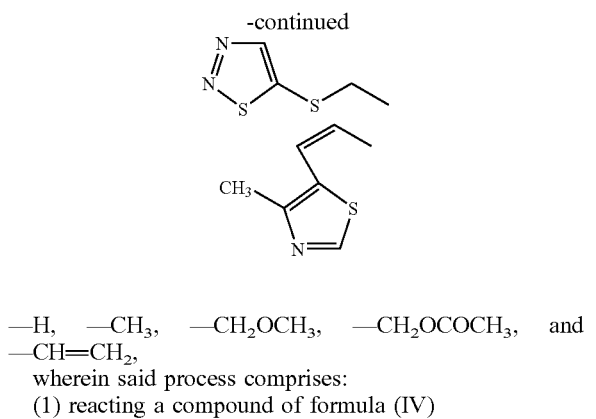

—H, —CH$_3$, —CH$_2$OCH$_3$, —CH$_2$OCOCH$_3$, and —CH=CH$_2$, wherein said process comprises:
(1) reacting a compound of formula (IV)

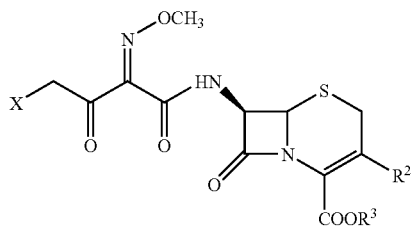

(IV)

wherein:
X is Cl or Br;
R$^2$ is as defined above; and
R$^3$ is hydrogen,
with benzathine or a salt thereof, to obtain crystals of a compound of formula (V)

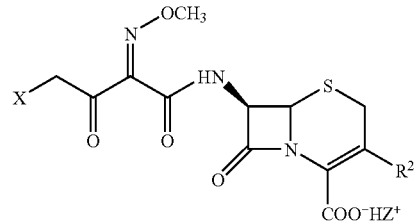

(V)

wherein:
Z is benzathine; and
X and R are as defined above;
(2) reacting said compound of formula (V) with thiourea, to obtain said compound of formula (I) or said pharmaceutically acceptable salt thereof.

In a preferred embodiment, R$^1$ is H or Na and R$^2$ is selected from the group consisting of

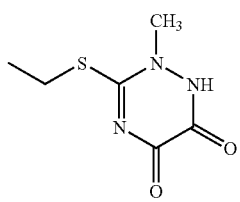

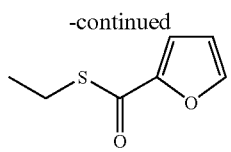

—H, —CH$_3$, —CH$_2$OCH$_3$, —CH$_2$OCOCH$_3$, and —CH=CH$_2$.

In another preferred embodiment, the compound of formula (V) is prepared by a process comprising:
(1) silylating a compound of formula (II)

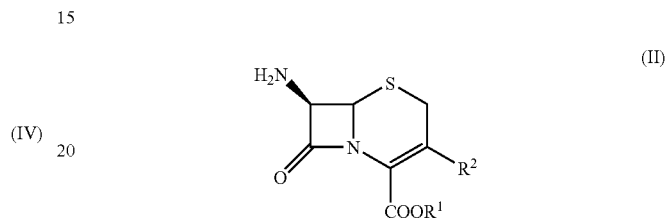

(II)

in which R$^2$ is as defined above, at the carboxyl to obtain the corresponding trialkylsilyl-ester which is reacted with a compound of formula (III)

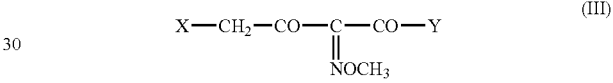

(III)

in which X is Cl or Br and Y is Cl, or —O—CH=N$^+$(CH$_3$)$_2$ Cl$^-$, to obtain a compound of formula (IV)

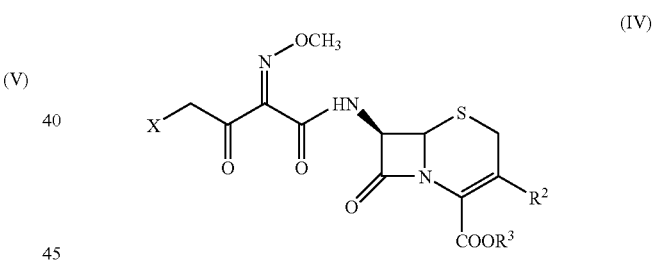

(IV)

wherein X and R$^2$ are as defined above, and R$^3$ is trialkylsilyl;
(2) hydrolyzing said compound of formula (IV) at a pH of 7 to 7.5, to obtain a hydrolyzed compound; and
(3) treating said hydrolyzed compound in a partly aqueous solution with benzathine or a salt thereof, to obtain crystals of a compound of formula (V).

In a particularly preferred process, the compounds of formula (I) are prepared by a process comprising:
(1) silylating a compound of formula (II)

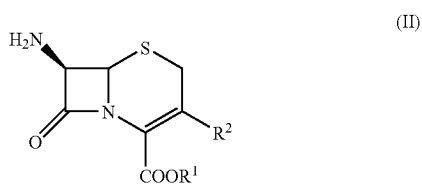

(II)

wherein R$^2$ is as defined above, to obtain the corresponding trialkylsilyl-ester;

(2) reacting said trialkylsilyl ester with a compound of formula (III)

$$X-CH_2-CO-\underset{\underset{NOCH_3}{\|}}{C}-CO-Y \quad (III)$$

wherein X is Cl or Br and Y is Cl, or —O—CH=N$^+$(CH$_3$)$_2$ Cl$^-$, to obtain a compound of formula (IV)

(IV)

[chemical structure of formula (IV) with OCH$_3$, N, HN, X, O, O, S, N, R$^2$, COOR$^3$]

wherein X and R$^2$ are as defined above, and R$^3$ is trialkylsilyl, (3) hydrolyzing said compound of formula (IV) at pH 7 to 7.5, to obtain a hydrolyzed compound;

(4) reacting said hydrolyzed compound in a partly aqueous solution with benzathine or a salt thereof, to obtain a salt of formula (V)

(V)

[chemical structure of formula (V) with OCH$_3$, N, HN, X, O, O, S, N, R$^2$, COO$^-$HZ$^+$]

wherein Z is benzathine and R$^2$ and X are as defined above, in which the carboxyl is salified by said benzathine;

(5) collecting said salt of formula (V) by filtration, to obtain a solid;

(6), washing said solid with water, to obtain a washed solid; and (7) reacting said washed solid in a partly aqueous solvent with thiourea, to obtain a solution of said compound of general formula (I) in which R$^2$ is as defined above and R$^1$ is H, said compound of formula (I) being crystallized from this solution in the form of the sodium salt, of the salt of a pharmaceutically acceptable inorganic acid or of an internal salt.

In these processes, the trialkylsilyl group may be any which is conventionally used as a protecting group. In a preferred embodiment, the trialkylsilyl group is tri-lower-alkylsilyl group, such as a triethylsilyl group or, even more preferably, a trimethylsilyl group. The silylation may be carried out with any reagent which is conventionally used to introduce a trialkylsilyl group, such as a trialkylhalosilane, including trialkylchlorosilanes, in particular tri-lower-alkylchlorosilanes, more preferably trimethylchlorosilane, or a N,O-bis-trialkylsilyl-acetamide, in particular a N,O-bis-tri-lower-alkylsilyl-acetamide, more preferably N,O-bis-trimethylsilyl-acetamide.

The present invention will now be exemplified in the context of specific cephalosporins. However, the same operative scheme can evidently be applied for the production of cephalosporins other than ceftiofur, cefotaxime and ceftriaxone, having nuclei different from the afore-specified three, but having the same 2-(2-aminothiazol-4-yl)-2-methoxyiminoacetic side chain in position 7.

EXAMPLES

Example 1

Preparation of Sodium Ceftiofur

Two separate solutions were prepared.

Solution A:

40 g of FURACA (MW 340.38; 0.118 moles) and 336 ml of tetrahydrofuran were fed into a dry 1 liter flask under a nitrogen flow in the absence of direct light. The mixture was agitated for 15 minutes until homogenization, while cooling in the meantime to +10° C.

While maintaining the temperature at +10° C. to +12° C., 1.486 ml of trimethylchlorosilane (MW 108.64; d=0.859; 0.1 eq) were quickly added. The mixture was agitated for 5 min at +10° C. to +12° C., and 45.43 g of N,O-bis-trimethylsilyl-acetamide (MW 203.43; d=0.832; 1.9 eq) were added over 5 to 10 minutes.

The temperature was raised to +20° C. and the mixture agitated for 1 hour 35 min at 22° C. to 23° C. until a solution was obtained. The solution was cooled to −35° C. to −40° C.

Solution B:

210 ml of ethyl acetate and 13.02 ml of N,N-dimethylformamide (MW 73.094; 0.169 moles; d=0.95; 12.37 g) were fed into a dry 1 liter flask under a nitrogen flow.

15.49 ml of phosphorus oxychloride (POCl$_3$) (0.167 moles; MW 153.33; d=1.675; 25.95 g) were added at +25° C., allowing the temperature to rise to +36° C.

The mixture was cooled to 0° C. and 27.62 g of 4-chloro-3-oxo-2-methoxyimino-butyric acid, commonly known as COMBA (MW 179.56; 0.154 moles) were added without exceeding+5° C. The mixture was agitated for 1 hour at +5° C.

Solution B was added dropwise to solution A over 15 minutes, while maintaining the temperature at −35° C. to −40° C. The reaction terminated within 2 hours at −35° C. to −40° C.

On termination of the reaction the mixture was poured into 500 ml of water at 0° C., while maintaining the pH at 7.0 to 7.5 with triethylamine, and while maintaining the temperature at 0° C.

200 ml of ethyl acetate were added, and the phases were separated at 0° C. to +5° C. Extraction was again effected at pH 7.0 to 7.5 with 350 ml of water.

The aqueous phase was decolorized at 0° C. to +5° C. for 30 minutes with 4 g of carbon and 0.4 g of EDTA. The aqueous phase was filtered and washed with 150 ml of water.

The pH was adjusted to 7.0 to 7.5 with triethylamine at 0° C. to +5° C. using a total of 110 ml thereof.

A mixture of 43.25 g of benzathine diacetate (0.120 moles) dissolved in 350 ml of water was added dropwise, then washed with 50 ml of water.

It was left to precipitate cold at 0° C. to +5° C. for about 90 minutes.

The precipitate was collected by filtration and washed with 500 ml of water divided into two portions.

It was left to drip well.

The condensation product of 7-FURACA with activated COMBA, precipitated moist as benzathine salt, was used as such in the next passage.

A sample was dried for analysis.

The moist benzathine salt obtained as described was suspended in 740 ml of tetrahydrofuran at +20° C. to +25° C.

It was cooled to 0° C. to +5° C., and 19 ml of triethylamine were added, while maintaining this temperature.

12 g of thiourea were added at 0° C. to +5° C., and the mixture was agitated for 18 hours.

The mixture was cooled to 0° C. to +5° C., and, while maintaining this temperature, 600 ml of ethyl acetate were added plus about 20 ml of concentrated hydrochloric acid to give a pH of 3. The precipitated benzathine hydrochloride was removed by filtration, and the filter washed with a mixture of 60 ml of tetrahydrofuran plus 60 ml of ethyl acetate.

400 ml of water were added to the filtrate solution.

The temperature was raised to +10° C. to +15° C., and the pH adjusted to 8.0 to 8.5 with 15 ml of triethylamine.

The phases were separated.

The impoverished organic phase was re-extracted with a further 400 ml of water at pH 8.0 to 8.5, and the aqueous phases were pooled and washed with 300 ml of ethyl acetate. 400 ml of tetrahydrofuran were added to the aqueous phase.

The mixture was cooled to 0° C. to +5° C., and the pH adjusted to 3 with 1N hydrochloric acid. 300 g of sodium chloride were added, and the mixture agitated until a solution formed, while raising the temperature to +15° C. to +20° C.

The phases were separated, the overlying organic phase being rich in product. Carbon was added to the organic phase at +15° C. to +20° C., and the mixture agitated for 20 minutes. The mixture was filtered and washed with 100 ml of tetrahydrofuran.

A homogeneous mixture of 28.88 g of sodium 2-ethylhexanoate and 100 ml of tetrahydrofuran was added dropwise to the decolorized organic phase over 20 minutes.

The mixture was agitated for 15 minutes at +15° C. to +20° C.

The solution obtained was added dropwise over 30 minutes to 1000 ml of agitated tetrahydrofuran at +20° C.

The mixture was agitated for 2 hours at +20° C., filtered and washed with 320 ml of acetone.

The product was dried at +30° C. to +32° C. to obtain 51.3 g of sodium ceftiofur.

The dried sample of benzathine salt had the following general formula (V), and more specifically has the general formula

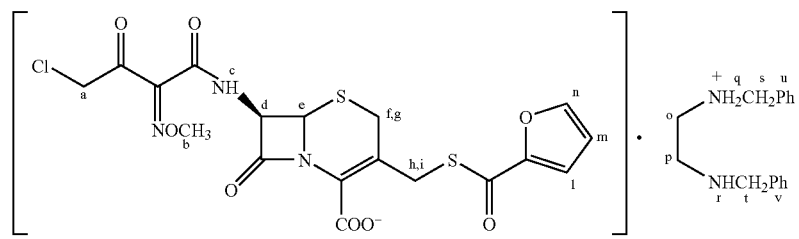

which provides the following spectra:

$^1$HNMR in DMSO-$d_6$ 300 Mhz; Hc=9.40 ppm 1H; Hn=8.04 ppm 1H; Hu-Hv=7.32–7.46 ppm 10H; H1=7.39 ppm 1H; Hm=6.77 ppm 1H; Hd=5.68 ppm 1H; He=5.06 ppm 1H; Hq-Hr=4.84 ppm 3H; Hb=3.95 ppm 3H; Hh-Hi=4.22–3.99 ppm 2H; Hf-Hg=3.65–3.26 ppm 2H; Hs-Ht=4.03 ppm 4H; Ho-Hp=2.95 ppm 4H; Ha=3.97 ppm 2H.

FT-IR (cm$^{-1}$); 1777.6-1717.1-1650.7-1565.8

Example 2

Preparation of Ceftriaxone Disodium Salt

Two separate solutions were prepared.

Solution A:

15.57 g of 7-ACT (MW 371.39; 0.042 mol) and 155 ml of methylene chloride were fed into a dry 1 liter flask under a nitrogen flow in the absence of direct light. The mixture was cooled to +10° C., and 34.11 g of N,O-bis-trimethylsilyl-acetamide were added, a slight amount of heat being produced. The mixture was agitated at +20 to 22° C., and after 45 minutes a complete solution was obtained. The mixture was cooled to –40° C.

Solution B:

80 ml of ethyl acetate and 4.69 ml of N,N-dimethylformamide (MW 73.09; d=0.95) were fed into a dry 1 liter flask under a nitrogen flow at +25° C. 5.58 ml of phosphorus oxychloride (MW 153.33; d=1.675; 9.34 g) were added allowing the temperature to rise to 36° C. (if this temperature is not attained within 20 to 25 minutes, heating is required). The mixture was cooled to 0° C., and then 9.94 g of 4-chloro-3-oxo-2-methoxyimino-butyric acid, commonly known as COMBA (MW 179.56) were added. The mixture is agitated at +5° C. for 1 hour.

Solution B was added dropwise to solution A over 15 to 20 minutes, while maintaining the temperature at –350 to –40° C. and washing the flask with 15 ml ethyl acetate. The mixture was agitated for 10 minutes at –35° to –40° C., and the reaction went to completion. The reaction mixture was poured into a mixture of 50 ml water, 320 ml isopropanol, and 270 ml of a saturated aqueous solution of sodium bicarbonate pre-cooled to 0° to –5° C. without exceeding +5° C. It was agitated for 2 hours at 0° to +5° C., while maintaining the pH at 2.5 (consuming about 27 ml of 17% hydrochloric acid), the pH being checked for about 90 minutes, during which any necessary correction is done with solid sodium bicarbonate. The phases were separated, and the underlying aqueous phase was retained. The rich organic phase was washed with 25 ml water, then with a solution of 22 g NaCl in 80 ml water. The aqueous phases were retained each time and pooled, then re-extracted with 40 ml methylene chloride. The organic phases were pooled, and the spent aqueous phase was discarded. The former was decolorized under agitation for 15 minutes with 1.5 g carbon, filtered and the filter cake was washed with 30 ml of methylene chloride. 150 ml of water were added to the decolorized organic phase at 0° to +5° C. followed by, still at 0° to +5° C., a solution of 11.21 g anhydrous sodium acetate in 100 ml water pre-cooled to 0° to +5° C. After 30 minutes, the phases were separated allowing the temperature to rise to about +20° C. The poor organic phase was re-extracted with 100 ml of water, facilitating separation with 50 ml of methylene chloride. The aqueous phases were pooled and decolorized at +20° C. for 30 minutes with 1.5 g of carbon, 0.150 g of EDTA and 0.200 g of celite. The mixture was filtered and the filter cake was washed with 100 ml water.

A solution of 15.14 g of benzathine diacetate in 160 ml demineralised water was added over 15 minutes to the decolorized solution at 150 to 20° C. The mixture was agitated for 30 minutes at 15° to 20° C., cooled to 0° to +5° C. and agitated for 1 hour. The mixture was filtered and washed 3 times with 50 ml of water. It was thoroughly squeezed under a nitrogen flow to obtain 28.52 g of the benzathine salt of the condensation product of 7-ACT with COMBA. A sample was dried for analysis.

The dried sample of benzathine salt had the general formula (V), and more specifically has the formula well-sifted crude ceftriaxone acid obtained above were added, then agitated at +10° C. for 4 hours until the dissolved ceftriaxone content remained constant. The resin was removed by filtration, washed with a mixture of 10 ml water plus 8 ml acetone and then with a mixture of 6 ml water and 19 ml acetone, maintaining these washes separate from the initial filtrate and at +10° C. The initial filtrate was maintained under agitation with 1.33 g carbon, 0.07 g EDTA and 0.13 g celite, for 45 minutes at +10° C. This mixture was filtered, and the filter cake was washed with the mixture of the two washes kept separate from the initial filtrate, the decolorized solution being diluted with 79.5 ml acetone added dropwise over 10 minutes at +10° C. The filtrate was seeded with disodium ceftriaxone and agitated for 90 minutes at +10° C. 291.5 ml of acetone were then added dropwise over 3 hours at +10° C. The product was collected by filtration and washed with 106 ml portions of acetone, thoroughly squeezed under a nitrogen flow then dried at ambient temperature until constant weight, to obtain 22.5 g disodium ceftriaxone.

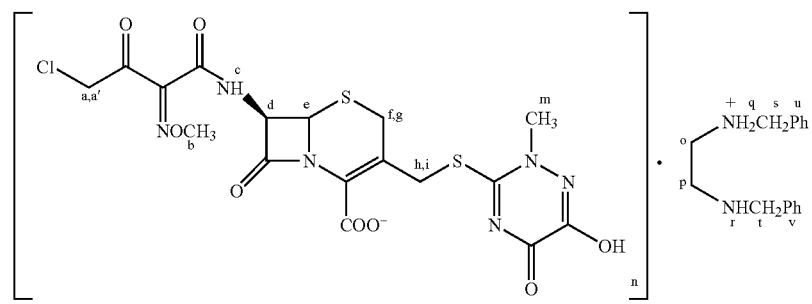

which provides the following spectra:

$^1$HNMR in DMSO-$d_6$ 300 MHz: Hc=9.36 ppm 1H; Hu-Hv=7.30–7.42 ppm 10H; Hd=5.65 ppm 1H; He=5.03 ppm 1H; Ha-Ha'=4.84 ppm 3H; Hb=4.03 ppm 3H; Hq-Hr=3.91 ppm 3H; Hh-Hi=4.35–4.12 ppm 2H; Hm=3.50 ppm 3H; Hf-Hg=3.62–3.39 ppm 2H; Hs-Ht=3.53 ppm 4H; Ho-Hp=2.89 ppm 4H.

FT-IR (cm$^{-1}$): 1775.1-1715.7-1666.6-1594.1

The benzathine salt obtained was suspended in 200 ml water and 142 g of the sulfonic resin Resindion UBK 530 in sodium form, and 6.38 g of thiourea were added at 20° to 25° C. The mixture was agitated for 4 hours at 20° to 25° C., filtered and washed 8 times with 50 ml of water each time, and then decolorized for 20 minutes at 15° to 20° C. with 1.5 g of carbon, 0.150 g of EDTA and 0.200 g of celite. The carbon was removed by filtration, and the filter cake was washed 4 times with 50 ml water. The pH was adjusted to about 4.2 with 7 ml of 17% hydrochloric acid at 15°/20° C., until precipitation began. It was agitated for 30 minutes, and adjusted to a pH of 3 over 40 minutes at 15° to 20° C. with about 13 ml of 17% hydrochloric acid.

The precipitate was collected by filtration, washed twice with 50 ml water, and thoroughly squeezed to obtain 45 g of crude ceftriaxone acid (K.F.=about 60%).

79.5 ml of acetone, 20 ml of water, 80 g of carboxylic resin RELITE CNS (activated in sodium form) were fed into a flask. The mixture was cooled to +10° C., and 45 g of Example 3

Preparation of Cefotaxime Sodium Salt

Two separate solutions were firstly prepared.

Solution A 64 g of 7-ACA (MW 272.28; 0.235 mol) and 400 ml of tetrahydrofuran were fed into a dry 1 liter flask under a nitrogen flow and in the absence of direct light. The mixture was agitated for 15 minutes until homogenized while cooling to +15° C.

191.34 g of N,O-bis-trimethylsilyl-acetamide (MW 203.43; d=0.832; 0.941 mol) were quickly added, maintaining the temperature at 200 to 25° C. The temperature was maintained at 200 to 25° C., while the mixture was agitated for 15 minutes at +20° to +25° C. until dissolved, then cooled to −35° C. to −40° C.

Solution B 420 ml of ethyl acetate and 26.04 ml of N,N-dimethyl-formamide (MW 73.09; d=0.95; 0.338 mol; 24.74 g) were fed into a dry 1 liter flask under a nitrogen flow at +25° C. 30.98 ml of phosphorus oxychloride (MW 153.33; d=1.675; 51.9 g) were added allowing the temperature to rise to 36° C. (if this temperature is not attained in 20 to 25 minutes, heating is required).

The mixture was cooled to 0° C. then, without exceeding +5° C., 55.24 g of 4-chloro-3-oxo-2-methoxyimino-butyric acid, commonly known as COMBA (MW 179.56; 0.308 mol) were added. The mixture was agitated at +5° C. for 1 hour.

Solution B was added dropwise into solution A over 15 to 20 minutes while maintaining the temperature at −350 to −40° C.

The reaction terminated within about 45 minutes at −35° to −40° C. At the end of the reaction, 600 ml of water at 0° C. were poured in, adjusting the pH to 7 to 7.5 with triethylamine and maintaining the temperature at 0° to +5° C.

The organic phase was extracted again with 450 ml of water at 0° to +5° C., while maintaining the pH at 7 to 7.5.

The aqueous phases were pooled, and a solution of 85.05 g of benzathine diacetate in 800 ml of water was added dropwise over 60 minutes, while maintaining the temperature at 0° to +5° C. The combined aqueous phase was agitated for 1 hour at 0° to +5° C., the product collected by filtration, and then washed twice with 250 ml water and thoroughly squeezed. 152 g of moist condensation product of 7-ACA with COMBA as the benzathine salt were obtained.

A sample was dried for analysis.

The dried sample of benzathine salt had the general formula (V) and more specifically has the formula

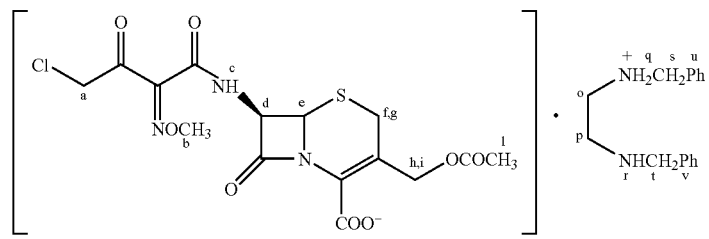

which provides the following spectra:

$^1$HNMR in DMSO-$d_6$ 300 MHz: Hc=9.42 ppm 1H; Hu-Hv=7.36–7.46 ppm 10H; Hd=5.73 ppm 1H; He=5.03 ppm 1H; Hq-Hr=4.85 ppm 3H; Hb=3.95 ppm 3H; Hh-Hi=4.11–4.03 ppm 2H;

Hf-Hg=3.55–3.36 ppm 2H; Hs-Ht=3.99 ppm 4H; Ho-Hp=3.05 ppm 4H; Ha=2.03 ppm 2H.

FT-IR (cm$^{-1}$): 1766.3-1719.5-1660.0-1555.8

The moist product obtained was suspended in a mixture of 320 ml of tetrahydrofuran and 80 ml of water, cooled to 0° to −5° C., and 22 ml of triethylamine were added to pH 7.5. 24.84 g of thiourea were added and left to react for 4 hours at +20° to +25° C., until conversion of the aforestated condensation product to cefotaxime was complete.

On termination of the reaction, 1.6 g of sodium hydrosulfite, 0.4 g of EDTA, 0.8 g of celite, and 4 g of carbon were added, and the mixture was agitated for 20 minutes, then filtered, and the product was washed with 80 ml of tetrahydrofuran. The tetrahydrofuran was evaporated under reduced pressure until an oily residue formed. 368 ml of water were added dropwise to the oil obtained under agitation.

233.6 g of 99% formic acid were dropped over a period of 5 to 10 minutes at +15° to +20° C. into the suspension obtained.

The resulting mixture was cooled to 0° to +5° C. and agitated for 3 hours, filtered, and the product washed with 96 ml of water pre-cooled to 0° to +5° C. The product was suspended in 384 ml of ethanol at 45 to 50° C. and agitated for 1 hour. The product was collected by filtration, while hot, and then washed with 192 ml of ethyl acetate.

After drying, 36 g of cefotaxime ethanol solvate with a concentration of 85% is obtained, serving as intermediate, was obtained.

227.5 ml of methanol, 28.2 ml of water, and 32.8 g of sodium 2-ethylhexanoate were fed into a flask under a nitrogen flow. The mixture was agitated at ambient temperature until completely dissolved and then cooled to 0° to +5° C. The intermediate cefotaxime acid ethanol solvate (87.5 g) was added, and complete dissolution was achieved at 0° to +5° C. The temperature was maintained, and 350 ml of ethyl acetate were added over 1 hour. The solution was seeded with cefotaxime sodium salt and agitated for 1 hour at 0° to +5° C. A further 263 ml of ethyl acetate were added over 40 minutes, and then a further 875 ml of ethyl acetate were added over 1 hour at 0° to 5° C. The mixture was agitated for 30 minutes at the same temperature, filtered, and the product washed with 88 ml ethyl acetate and dried at 30° C. under reduced pressure. Yield: 80.5 g of cefotaxime sodium salt.

Example 4

Preparation of Ceftiofur Hydrochloride

Two separate solutions were prepared.

Solution A:

20 g of Furaca (MW 340.38; 58.76 mmol) and 168 ml of tetrahydrofuran were fed into a dry 1 liter flask under a nitrogen flow and in the absence of direct light. The mixture was agitated for 15 minutes until homogenized while cooling to +10° C. At +10° to +12° C., 0.743 ml of trimethylchlorosilane (MW 108.64; d=0.859) were quickly added. The mixture was agitated for 5 minutes at +10° to +12° C. and then 22.72 g of BSA (MW=203.43) were added over 5 to 10 minutes.

The temperature was raised to +20° C., and the mixture was agitated for 95 minutes at +22° to +23° C. until completely dissolved. It was then cooled to −35° to −40° C.

Solution B:

105 ml of ethyl acetate and 6.51 ml of dimethylformamide (MW 73.09; d=0.95) were fed into a dry 1 liter flask under a nitrogen flow. At a temperature of +25° C., 7.75 ml of POCl$_3$ (MW 153.33; d=1.675) were added, allowing the temperature to rise to +36° over 20 to 25 minutes, if necessary heating it slightly. The mixture was cooled to 0°

C., and then 13.81 g of 4-chloro-3-oxo-2-methoxyiminobutyric acid, commonly known as COMBA (MW 179.56) were added taking care not to exceed+5° C. Agitation was maintained at +5° C. for 60 minutes.

Solution B was added dropwise into solution A over 15 minutes, while maintaining the temperature at −35° to −40° C.

The mixture was left to react for 2 hours at the same temperature.

On termination of the reaction, the reaction mixture was poured into 100 ml of iced water, while correcting the pH to 3.0 with about 20 ml of triethylamine and maintaining the temperature at 0° to +5° C. The temperature was raised to +15° to +20° C., and the phases were separated. The aqueous phase was again extracted with 100 ml of ethyl acetate, and the organic phases were pooled and decolorized with 2 g of carbon, while maintaining agitation for 20 minutes at 15° to 20° C. The latter was removed by filtration, and the filter cake was washed with 25 ml of tetrahydrofuran and then with 25 ml of ethyl acetate.

The solution was cooled to 0° to +5° C., and 200 ml water at 0° to+5° C. were added. At the same temperature, the pH was corrected to 8 with about 13 ml of triethylamine.

The phases were separated and extracted twice more with 100 ml water, while maintaining the pH at 8 with 3 ml of triethylamine. The aqueous phases were pooled and a solution of benzathine diacetate (27.75 g; MW 360.4) in 262.5 ml water was added dropwise over 30 minutes, at 0° to +5° C., then the remaining benzathine solution left in the dropping funnel was recovered, and washed with water (37.5 ml). Agitation was maintained for 2 hours at 0° to +5° C., then the product was collected by filtration and allowed to drain well, then finally washed 4 times, each time with 50 ml of water. 112 g of intermediary product as moist benzathine salt were obtained, with a K.F. of about 60%.

The moist product with the afore-stated K.F. was suspended in tetrahydrofuran (250 ml) at +20° to 25° C. 200 g of UBK530 resin in sodium form and 5.86 g of thiourea were added in the stated order to the suspension obtained, the pH then being corrected to 8.0 to 8.5 with triethylamine (2.5 ml).

Agitation was maintained for 3 hours at 20° to 25° C., then further triethylamine (3.5 ml) was added to correct the pH to 7.5 to 8.0. After further agitation for 20 hours at 20° to 25° C., a final reaction pH of 2.5 to 3.0 was achieved. The resin was removed by filtration and washed with 2×50 ml portions of tetrahydrofuran, then twice with a mixture of 25 ml tetrahydrofuran plus 25 ml of ethyl acetate and finally with 25 ml of water.

Triethylamine (7.5 ml) was added to achieve a pH of 8.0 to 8.5, and then ethyl acetate (200 ml) was added. The phases were separated, and the aqueous phase was decolorized with 2 g of carbon, adding 0.2 g of EDTA and 0.2 g of celite and agitating for 20 minutes.

The organic phase was re-extracted with 100 ml of water, which was used to wash the filter cake following decolorization, whereas the organic phase was finally removed.

125 ml of tetrahydrofuran were added to the decolorized aqueous phase, cooled to 0° to +5° C., and the pH corrected to 3 with about 60 ml of 1N HCl. 50 g of sodium chloride were then added at the same temperature, the mixture was heated to +15° to +20° C., and the phases were separated.

Water (250 ml) was added to the organic phase, and the pH was adjusted to 8.0 to 8.5 with triethylamine (about 12.5 ml), then ethyl acetate (250 ml) was added.

The phases were again separated, and the organic phase was re-extracted with water (150 ml) at pH 8.0 to 8.5 The aqueous phases were pooled, washed 3 times with ethyl acetate (200 ml each time), and the aqueous phase was decolorized with 2 g of carbon plus 0.2 g EDTA plus 0.2 g celite.

The decolorized aqueous phase was filtered and washed with water (100 ml), and the resulting solution was cooled to 0° to +5° C., and the pH was adjusted to 3 with about 48 ml of 1N HCl. The mixture was agitated while cold for 1 hour, and the product was collected by filtration and washed twice with 100 ml water. The product was left to drip well under nitrogen, to obtain 114 g of moist product.

The moist solid was suspended in tetrahydrofuran (125 ml) and agitated at 20° C. until dissolution is virtually complete, after about 30 minutes, then a saturated aqueous solution (50 ml) of sodium chloride was added and further agitated until complete homogenisation of the mixture.

The phases were separated. The organic phase was decolorized with 2 g carbon at 20° C., filtered and washed with 50 ml tetrahydrofuran. It was cooled to 0° to +5° C., the pH was corrected to 0.5 with concentrated HCl (about 5.5 ml) and maintained under agitation for 10 minutes at 0° to +5° C.

The acid solution was added dropwise over 45 minutes to 1500 ml acetone while agitated at 20° C. Agitation was continued for a further 60 minutes at 20° C., then the mixture was cooled to 0°/+5° C. and again agitated for a further 60 minutes. The product was collected by filtration and washed with 150 ml acetone to obtain 29 g of moist product.

The product was dried at 20° C. to obtain 20.5 g of ceftiofur hydrochloride.

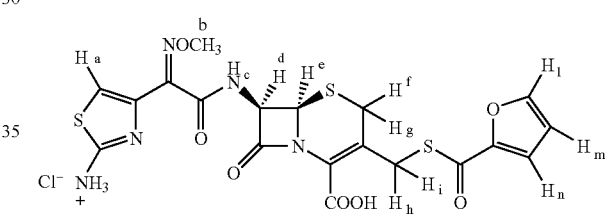

Ceftiofur Hydrochloride $^1$HNMR:
9.79 ppm doublet Jcd=8.1 Hz Hc
8.06 ppm Hn ddd system abc
7.44 ppm Hm ddd system abc
6.91 ppm Hl ddd system abc
6.76 ppm singlet Ha
5.76 ppm Hd dd Jcd=8.1, Jde=5.16 Hz
5.16 ppm He doublet Jde=5.16 Hz
4.27 ppm, 3.93 ppm Hh, Hi system ab two doublets Jhi=13.2 Hz
3.74 ppm, 3.38 ppm Hf, Hg two doublets system ab Jfg=17.6 Hz
3.92 ppm Hb singlet Ceftiofur Hydrochloride FT-IR
amide NH stretching 3273 cm$^{-1}$
lactam C=O 1766.3 cm$^{-1}$
thioester C=O 1709.0 cm$^{-1}$
carboxyl C=O 1659.4 cm$^{-1}$
amide C=O 1629.4 cm$^{-1}$ Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A process for preparing a compound of formula (I):

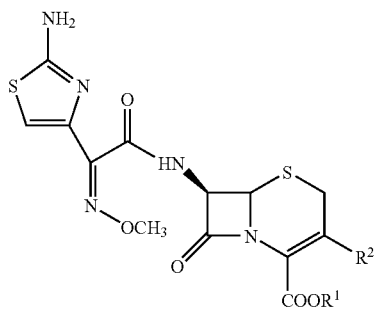

wherein:
R¹ is H; and
R² is selected from the group consisting of

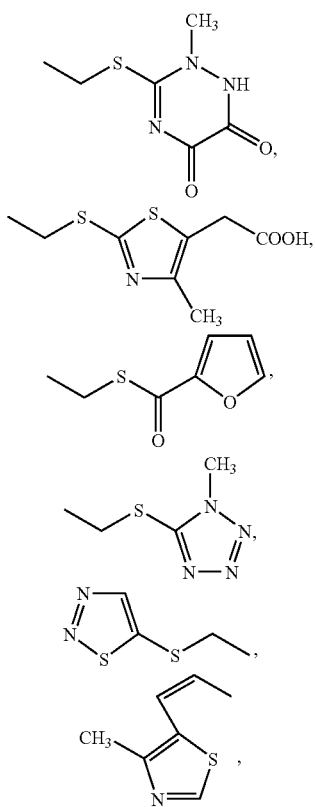

—H, —CH₃, —CH₂OCH₃, —CH₂OCOCH₃, and —CH=CH₂, wherein said process comprises:
(1) reacting a compound of formula (IV):

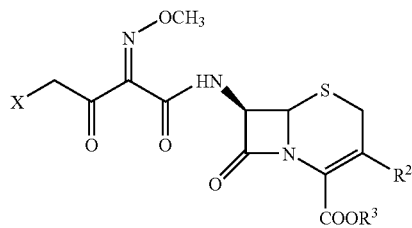

wherein:
X is Cl or Br;
R² is as defined above; and
R³ is hydrogen, with benzathine or a salt thereof, to obtain crystals of a compound of formula (V):

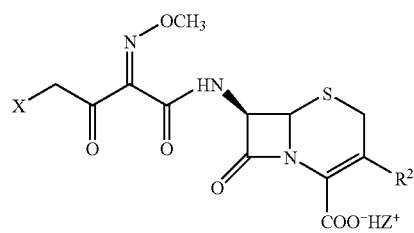

wherein:
Z is benzathine; and
X and R² are as defined above; and
(2) reacting said compound of formula (V) with thiourea, to obtain said compound of formula (I).

2. The process of claim 1, further comprising:
(3) crystallizing said compound of formula (I).

3. The process of claim 1, wherein R² is selected from the group consisting of

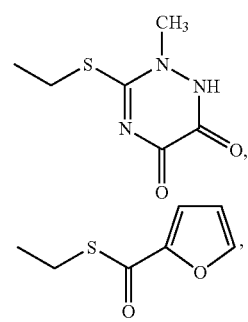

—H, —CH₃, —CH₂OCH₃, —CH₂OCOCH₃, and —CH=CH₂.

4. The process of claim 3, further comprising:
(3) crystallizing said compound of formula (I).

5. A compound of formula (V):

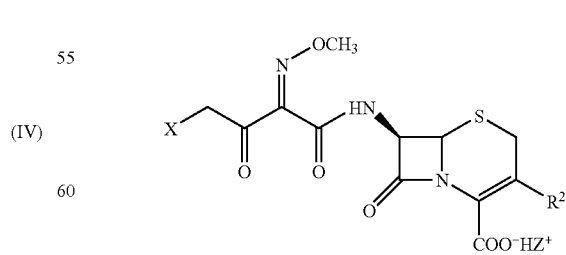

wherein:
Z is benzathine;
X is Cl or Br; and $R^2$ is selected from the group consisting of

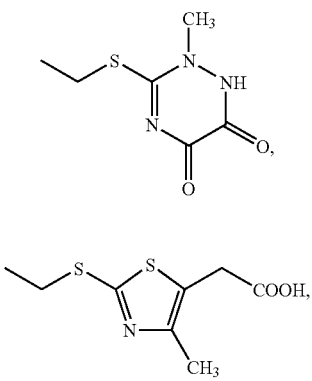

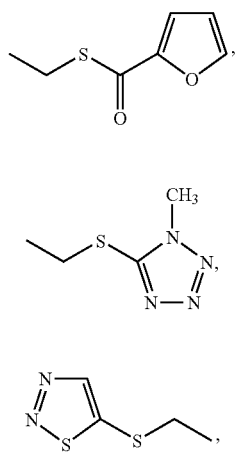

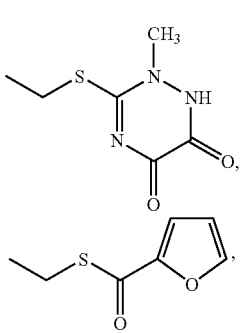

—H, —CH₃, —CH₂OCH₃, —CH₂OCOCH₃, and —CH=CH₂.

6. The compound of formula (V) of claim 5, wherein $R^2$ is selected from the group consisting of —H, —CH₃, —CH₂OCH₃, —CH₂OCOCH₃, and —CH=CH₂.

7. A process for preparing a compound of formula (V):

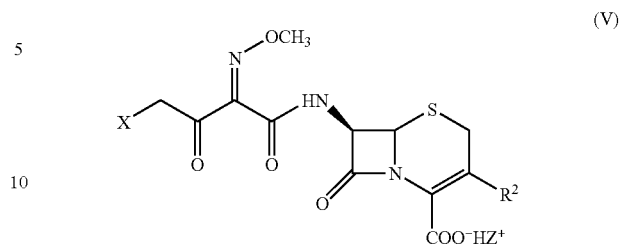

wherein:
Z is benzathine;
X is Cl or Br; and
$R^2$ selected from the group consisting of —H, —CH₃, —CH₂OCH₃, —CH₂OCOCH₃, and —CH=CH₂,
wherein said process comprises:
(1) reacting a compound of formula (IV):

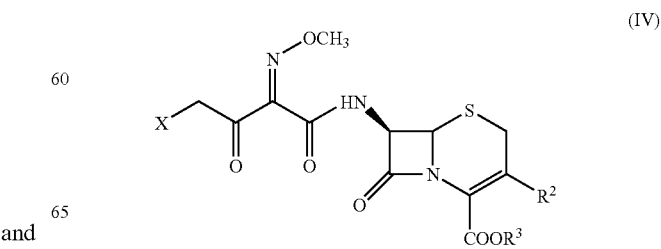

wherein X and R² are as defined above, and R³ is hydrogen, with benzathine or a salt thereof, to obtain said compound of formula (V).

8. The process of claim 7, comprising:
(1) silylating a compound of formula (II):

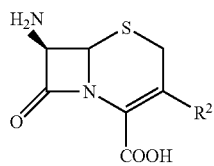
(II)

wherein R² is selected from the group consisting of

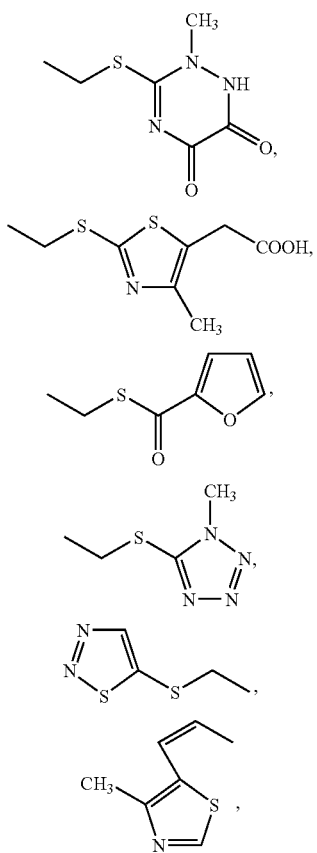

—H, CH₃, —CH₂OCH₃, —CH₂OCOCH₃, and —CH=CH₂, at the carboxyl to obtain the corresponding trialkylsilyl-ester which is reacted with a compound of formula (III):

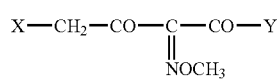
(III)

wherein X is Cl or Br and Y is Cl, or —O—CH=N⁺(CH₃)₂ Cl⁻, to obtain a compound of formula (IV):

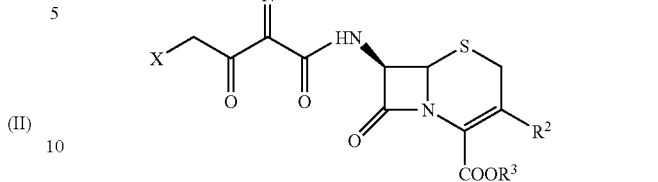
(IV)

wherein X and R² are as defined above, and R³ is trialkylsilyl;
(2) hydrolyzing said compound of formula (IV) at a pH of 7 to 7.5, to obtain a hydrolyzed compound; and
(3) treating said hydrolyzed compound in an aqueous solution with benzathine or a salt thereof, to obtain crystals of a compound of formula (V).

9. A process for preparing a cephalosporin of formula (I) or a pharmaceutically acceptable salt thereof

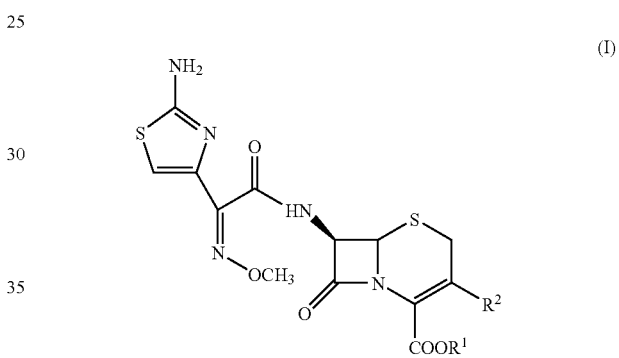
(I)

wherein:
R¹ is H or Na; and
R² is selected from the group consisting of

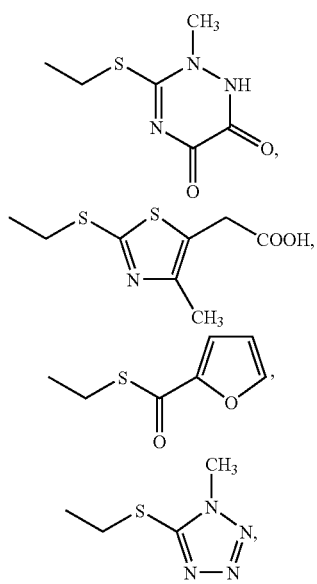

—H, —CH$_3$, —CH$_2$OCH$_3$, —CH$_2$OCOCH$_3$, and —CH=CH$_2$;

wherein said process comprises:

(1) silylating a compound of formula (II):

(II)

wherein R$^2$ is as defined above, to obtain the corresponding trialkylsilyl-ester;

(2) reacting said trialkylsilyl ester with a compound of formula (III):

X—CH$_2$—CO—C(=NOCH$_3$)—CO—Y  (III)

wherein X is Cl or Br and Y is Cl, or —O—CH=N$^+$(CH$_3$)$_2$ Cl$^-$, to obtain a compound of formula (IV):

(IV)

wherein X and R$^2$ are as defined above, and R$^3$ is trialkylsilyl;

(3) hydrolyzing said compound of formula (IV) at pH 7 to 7.5, to obtain a hydrolyzed compound;

(4) reacting said hydrolyzed compound in an aqueous solution with benzathine or a salt thereof, to obtain a salt of formula (V):

(V)

wherein Z is benzathine and R$^2$ and X are as defined above, in which the carboxyl is salified by said benzathine;

(5) collecting said salt of formula (V) by filtration, to obtain a solid;

(6), washing said solid with water, to obtain a washed solid; and (7) reacting said washed solid in an aqueous solvent with thiourea, to obtain a solution of said compound of formula (I) in which R$^2$ is as defined above and R$^1$ is H, said compound of formula (I) being crystallized from this solution in the form of the sodium salt, of the salt of a pharmaceutically acceptable inorganic acid or of an internal salt.

10. The process of claim 9, wherein said reacting with thiourea is accompanied by the precipitation of benzathine hydrochloride and said benzathine hydrochloride is removed by filtration to obtain a solution of the compound of formula (I).

11. The process of claim 9, wherein R$^2$ is selected from the group consisting of —H, —CH$_3$, —CH$_2$OCH$_3$, —CH$_2$OCOCH$_3$, and —CH=CH$_2$.

12. The process of claim 10, wherein R$^2$ is selected from the group consisting of —H, —CH$_3$, —CH$_2$OCH$_3$, —CH$_2$OCOCH$_3$, and —CH=CH$_2$.

* * * * *